(12) United States Patent
Van Steenberge et al.

(10) Patent No.: US 9,453,799 B2
(45) Date of Patent: Sep. 27, 2016

(54) OPTICAL FLUORESCENCE-BASED CHEMICAL AND BIOCHEMICAL SENSORS AND METHODS FOR FABRICATING SUCH SENSORS

(71) Applicants: IMEC, Leuven (BE); Universiteit Gent, Ghent (BE)

(72) Inventors: Geert Van Steenberge, St. Amandsberg (BE); Sandeep Kalathimekkad, Kerala (IN); Jeroen Missinne, Ghent (BE)

(73) Assignees: IMEC, Leuven (BE); Universiteit Gent, Ghent (BE)

( * ) Notice: Subject to any disclaimer, the term of this patent is extended or adjusted under 35 U.S.C. 154(b) by 0 days.

(21) Appl. No.: 14/289,424

(22) Filed: May 28, 2014

(65) Prior Publication Data

US 2014/0319378 A1    Oct. 30, 2014

Related U.S. Application Data

(63) Continuation of application No. PCT/EP2012/076239, filed on Dec. 19, 2012.

(60) Provisional application No. 61/578,653, filed on Dec. 21, 2011.

(51) Int. Cl.
*G01N 21/77*    (2006.01)
*G01N 21/64*    (2006.01)

(52) U.S. Cl.
CPC ...... *G01N 21/7703* (2013.01); *G01N 21/6428* (2013.01); *G01N 21/6452* (2013.01); *G01N 2021/7713* (2013.01)

(58) Field of Classification Search
CPC ................ G01N 21/6428; G01N 2021/7713; G01N 21/7703
See application file for complete search history.

(56) References Cited

U.S. PATENT DOCUMENTS

| | | | |
|---|---|---|---|
| 5,249,251 A | 9/1993 | Egalon et al. | |
| 5,910,661 A * | 6/1999 | Colvin, Jr. | 250/573 |
| 6,051,437 A * | 4/2000 | Luo et al. | 436/172 |
| 2003/0133639 A1 | 7/2003 | Tao et al. | |
| 2004/0245660 A1 | 12/2004 | Ohtsu et al. | |
| 2007/0116607 A1* | 5/2007 | Wang et al. | 422/83 |
| 2009/0068668 A1* | 3/2009 | Duer | 435/6 |

(Continued)

FOREIGN PATENT DOCUMENTS

WO    WO 2013/092766    6/2013

OTHER PUBLICATIONS

Klunder, et al., "Core-Based Intrinsic Fiber-Optic Absorption Sensor for the Detection of Volatile Organic Compounds," Applied Spectroscopy, 1995, vol. 49, No. 3, pp. 379-385.

(Continued)

*Primary Examiner* — David Porta
*Assistant Examiner* — Hugh H Maupin
(74) *Attorney, Agent, or Firm* — Knobbe Martens Olson & Bear LLP (57) ABSTRACT

An optical fluorescence-based sensor comprising at least one sensing element is disclosed. In one aspect, the at least one sensing element comprises a waveguide comprising a waveguide core, a light source optically coupled to an input part of the waveguide core, and a photodetector optically coupled to an output part of the waveguide core, the waveguide core being made of a material comprising a mixture of an optical material and a fluorescent dye.

16 Claims, 5 Drawing Sheets

(56) References Cited

U.S. PATENT DOCUMENTS

2009/0166903 A1    7/2009  Kim et al.
2009/0202193 A1    8/2009  Foerster et al.

OTHER PUBLICATIONS

Bliss, et al., "Integrated wavelength-selective optical waveguides for microfluid-based laser-induced fluorescence detection," The Royal Society of Chemistry 2008, Oct. 2007, vol. 8, pp. 143-151.

Courbat, et al., "Colorimetric gas sensors based on optical waveguides made on plastic foil," Procedia Chemistry I, 2009, pp. 576-579.

Burke, et al., "Development of an integrated optic oxygen sensor using a novel, generic platform," The Royal Society of Chemistry 2005, Nov. 2004, vol. 130, pp. 41-45.

Blyler, et al., "Optical Fiber Chemical Sensors Utilizing Dye-Doped Silicone Polymer Claddings," Polymer Engineering and Science, 1989, vol. 29, No. 17, pp. 1215-1218.

Enami, et al., "Detection of organophosphorus compound based on a sol-gel silica planar waveguide doped with a green fluorescent protein and an organophosphorus hydrolase," Applied Physics Letters, Jun. 7, 2011, vol. 98, pp. 233503-1-233503-3.

Kalathimekkad et al., "Fluoresence-based optochemical sensor on flexible foils," Proc. of SPIE, 2012, vol. 8439, pp. 84390Y-1-84390Y-9.

Llobera et al., "Full-field photonic biosensors based on tunable bio-doped sol-gel glasses," The Royal Society of Chemistry 2008, May 2008, vol. 8, pp. 1185-1190.

International Search Report dated Apr. 29, 2013, in International Application No. PCT/EP2012/076239.

\* cited by examiner

OPTICAL FLUORESCENCE-BASED CHEMICAL AND BIOCHEMICAL SENSORS AND METHODS FOR FABRICATING SUCH SENSORS

CROSS REFERENCE TO RELATED APPLICATIONS

This application is a continuation of PCT Application No. PCT/EP2012/076239, filed Dec. 19, 2012, which claims priority under 35 U.S.C. §119(e) to U.S. Provisional Patent Application No. 61/578,653, filed Dec. 21, 2011. Each of the above applications is hereby incorporated by reference in its entirety.

BACKGROUND

1. Technological Field

The disclosed technology relates to optical fluorescence-based, for example chemical and biochemical, sensors for example suitable for multi-analyte detection and to methods for fabricating such sensors.

2. Description of the Related Technology

Fluorescence-based gas sensors offer a high sensitivity and ease of operation. In addition, they offer the possibility of remote monitoring. Despite the availability of various schemes of fluorescence-based gas sensor platforms, a low-cost, flexible, compact and robust platform for multi-analyte detection still remains to be explored. In "Colorimetric gas sensors based on optical waveguides made on plastic foil," Procedia Chemistry 1 (2009) 576-579, J. Courbat et al. report on the realization of a lowcost polymeric optical waveguide made on a plastic foil and used for colorimetric gas detection. The transducer concept is based on a planar optical waveguide made of a PET foil combined with surface mount device optical components (LEDs and photodiodes). Light coupling between the LEDs and the waveguide and between the waveguide and the photodiodes is realized by means of micromirrors formed on the PET foil. Gas sensing is based on the detection of variations in the light absorption in the evanescent field of a colorimetric film deposited on the plastic foil and sensitive to a specific gas to be detected. The light intensity that reaches the photodiode depends on the absorption of light in the evanescent field going along the colorimetric film. In this approach, the interaction of light with the sensing material is only through evanescent waves.

In "Development of an integrated optic oxygen sensor using a novel, generic platform," Analyst (2005), 130(1): 41-45, C. S. Burke et al. describe the development of a generic platform for enhanced, integrated optic sensors based on fluorescence detection. The platform achieves enhanced performance and has inherent multi-analyte detection capability. The sensor chip comprises a ridge waveguide array on a planar substrate. Spots of fluorescent material sensitive to an analyte are deposited on one end of each waveguide and these spots are excited directly using a (non-integrated) LED source. The resulting fluorescence is coupled into the waveguides and propagates along their length to be detected at their respective endfaces by an appropriate detector. Direct excitation is an important design feature of the sensor chip as it is considerably more efficient than evanescent-wave excitation. In this approach the sensing area is limited, as it corresponds to the area of the fluorescent spots (having a diameter of e.g. 60 micrometer). Also, the output intensity distribution at the waveguide endface exhibits a strong angular peak, which dictates the optimal detector orientation out of the plane of the waveguide. This approach may be less suitable for fabricating integrated, planar sensors.

SUMMARY OF CERTAIN INVENTIVE ASPECTS

Certain inventive aspects relate to optical fluorescence-based chemical and biochemical sensors that are suitable for multi-analyte detection, wherein the sensors are based on direct excitation of fluorescent dyes, wherein the sensors have a large sensing area and wherein the sensors are compact, flexible and stretchable. Certain inventive aspects relate to methods for fabricating such optical fluorescence-based chemical and biochemical sensors using low-cost materials and simple fabrication techniques.

One inventive aspect relates to optical fluorescence-based chemical and biochemical sensors comprising at least one sensing element, the at least one sensing element comprising a waveguide comprising a waveguide core, a light source optically coupled to an input part of the waveguide core and a photodetector optically coupled to an output part of the waveguide core. The waveguide core is made of a material comprising a mixture of an optical material and a fluorescent dye, wherein the fluorescent dye is sensitive to an analyte to be detected. The at least one sensing element may further comprise an optical filter in between the output part of the waveguide core and the photodetector, the optical filter being provided for filtering out undesired wavelengths. The sensor may further comprise electrical circuitry.

In operation, light is emitted from the light source and coupled into the waveguide core of a sensing element. The light source is selected such that it emits light in a first wavelength range within or overlapping with the excitation spectrum of the fluorescent dye present in the corresponding waveguide core. The fluorescent dye absorbs light of the first wavelength or first wavelength range and re-emits part of the absorbed energy at a second wavelength or in a second wavelength range different from the first wavelength range. In one aspect, the optical material, e.g. optical silicone, used for forming the waveguide core is a porous material allowing penetration of an analyte to be detected through the pores towards the fluorescent dye. Thus, upon diffusion of an analyte to be detected into the pores of the waveguide core, the emission spectrum of the fluorescent dye changes. This change in emission spectrum comprises a shift in dye emission wavelengths and/or a change in emitted optical energy (total emitted energy or energy emitted at a specific wavelength or energy emitted within a specific wavelength range). This change is detected by the photodetector. The photodetector is selected such that it is sensitive in a wavelength range corresponding to the emission spectrum of the fluorescent dye in the corresponding waveguide core.

A sensor according to one aspect may comprise a plurality of sensing elements. For example, each of the sensing elements may comprise a different fluorescent dye, thus enabling multi-analyte detection. For example, in each of the sensing elements a same fluorescent dye with a different dye concentration can be used. For example, each of the sensing elements may comprise a same fluorescent dye and a different optical filter.

The optical material of the waveguide core can comprise an optical silicone. It is an advantage of optical silicones that they are porous, thus enabling penetration of analytes into the waveguide core. In addition, optical silicones are highly transparent in the UV-region down to about 350 nm. Therefore a large range of wavelengths can be used for sensing, and thus a large variety of fluorescent dyes operating at different wavelengths can be used. Optical silicones also have a potential for bio-compatibility. However, the present disclosure is not limited thereto and other materials such as for example an acrylic material (such as e.g. Di(trimethylolpropane)tetraacrylate) may be used as an optical material for the waveguide core.

In one aspect, optical coupling of a light source to an input part of the waveguide core can be done by means of a first coupling element such as a micromirror, a prism or a grating structure. Alternatively, a side-emitting light source can be used that can be coupled directly to the input part of the waveguide core.

In one aspect, optical coupling of a photodetector to an output part of the waveguide core can be done by means of a second coupling element such as a micromirror, a prism or a grating structure.

In one aspect, the optical filter between the output part of the waveguide core and the photodetector may comprise a multilayer filter being provided at a light receiving side of the photodetector. In one aspect, the optical filter between the output part of the waveguide core and the photodetector may be formed by incorporating a wavelength selective absorbing dye acting as a filter at an output part of the waveguide core.

It is an advantage of a sensor according to one aspect that it can be made using flexible and stretchable materials such as for example PDMS (polydimethylsiloxane), such that the sensor can be flexible and stretchable.

It is an advantage of a sensor according to one aspect that it can be made of materials not exhibiting auto-fluorescence or exhibiting very low auto-fluorescence, such as for example PDMS. Therefore the characteristics (such as e.g. response, sensitivity, . . . ) of such a sensor are only dependent on the properties of the dye material and not on the properties of the core material.

It is an advantage of a sensor according to one aspect that the fluorescent dye is mixed with the waveguide core material. This enables a large interaction area with the analyte to be detected, i.e. a large sensing area, possibly leading to a high sensitivity and a good signal to noise ratio.

It is an advantage of a sensor according to one aspect that the light source and the photodetector can be well integrated with the waveguide, thus leading to compact sensing systems.

One inventive aspect relates to methods for fabricating optical fluorescence based chemical and biochemical sensors. A fabrication method in one aspect allows using low-cost materials and simple fabrication techniques.

A method of fabricating a chemical or biochemical sensor comprising a plurality of sensing elements according to one aspect comprises: providing a master mold comprising a pattern corresponding to the pattern of the plurality of waveguide cores to be formed; fabricating a patterned substrate using the master mold as a template; bonding the patterned substrate to a plane substrate, thereby forming a plurality of channels between the patterned substrate and the plane substrate; filling the plurality of channels with a material comprising a mixture of an optical material and a fluorescent dye; curing the material, thereby forming a plurality of waveguide cores.

The patterned substrate can be made of a flexible and/or stretchable material such as for example a silicone, e.g. PDMS (polydimethylsiloxane). Fabricating the patterned substrate using the master mold as a template can comprise providing a layer of silicone on the master mold, curing the silicone layer and peeling off the cured layer from the master mold.

The method may further comprise removing the plane substrate. In other embodiments the plane substrate may remain as part of the sensor, e.g. forming a cladding layer.

The method may further comprise integrating a plurality of light sources and optically coupling each light source to an input part of a waveguide core by means of a first coupling element such as for example a micromirror, a grating or a prism. The method may further comprise integrating a plurality of photodetectors and optically coupling each photodetector to an output part of a waveguide core by means of a second coupling element such as for example a micromirror, a grating or a prism.

Certain objects and advantages of various inventive aspects have been described herein above. Of course, it is to be understood that not necessarily all such objects or advantages may be achieved in accordance with any particular embodiment of the disclosure. Thus, for example, those skilled in the art will recognize that the disclosure may be embodied or carried out in a manner that achieves or optimizes one advantage or group of advantages as taught herein without necessarily achieving other objects or advantages as may be taught or suggested herein. Further, it is understood that this summary is merely an example and is not intended to limit the scope of the disclosure. The disclosure, both as to organization and method of operation, together with features and advantages thereof, may best be understood by reference to the following detailed description when read in conjunction with the accompanying drawings.

BRIEF DESCRIPTION OF THE DRAWINGS

In the different drawings, the same reference signs refer to the same or analogous elements.

DETAILED DESCRIPTION

In the following detailed description, numerous specific details are set forth in order to provide a thorough understanding of the disclosure and how it may be practiced in particular embodiments. However, it will be understood that the present disclosure may be practiced without these specific details. In other instances, well-known methods, procedures, and techniques have not been described in detail, so as not to obscure the present disclosure. While the present disclosure will be described with respect to particular embodiments and with reference to certain drawings, the disclosure is not limited hereto. The drawings included and described herein are schematic and are not limiting the scope of the disclosure. It is also noted that in the drawings, the size of some elements may be exaggerated and, therefore, not drawn to scale for illustrative purposes.

Furthermore, the terms first, second, third, and the like in the description and in the claims, are used for distinguishing between similar elements and not necessarily for describing a sequence, either temporally, spatially, in ranking, or in any other manner. It is to be understood that the terms so used are interchangeable under appropriate circumstances and that the embodiments of the disclosure described herein are capable of operation in other sequences than described or illustrated herein.

Moreover, the terms top, bottom, over, under, and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

It is to be noticed that the term "comprising," used in the claims, should not be interpreted as being restricted to the means listed thereafter; it does not exclude other elements or steps. It is thus to be interpreted as specifying the presence of the stated features, integers, steps, or components as referred to, but does not preclude the presence or addition of one or more other features, integers, steps, or components, or groups thereof. Thus, the scope of the expression "a device comprising means A and B" should not be limited to devices consisting only of components A and B.

In the context of the present disclosure, an analyte is an element or a substance to be detected, such as a gas, a vapor, or a liquid.

In the context of the present disclosure, flexible means non-stiff, non-rigid, i.e. bendable but not stretchable. A flexible structure is adapted to be deformable in a certain direction during normal use of the structure, but does not elongate. The length does not change during bending.

In the context of the present disclosure, stretchable means resilient, i.e. elastically deformable with elongation. A stretchable structure is adapted to be elastically deformed during normal use (with elongation).

One embodiment provides optical fluorescence-based chemical and biochemical sensors that are suitable for multi-analyte detection. The sensors of one embodiment have a high sensitivity, they are compact (fully integrated) and they can be flexible and/or stretchable. One embodiment further provides methods for fabricating such optical fluorescence-based chemical and biochemical sensors using low-cost materials and simple fabrication techniques.

Figure 1:
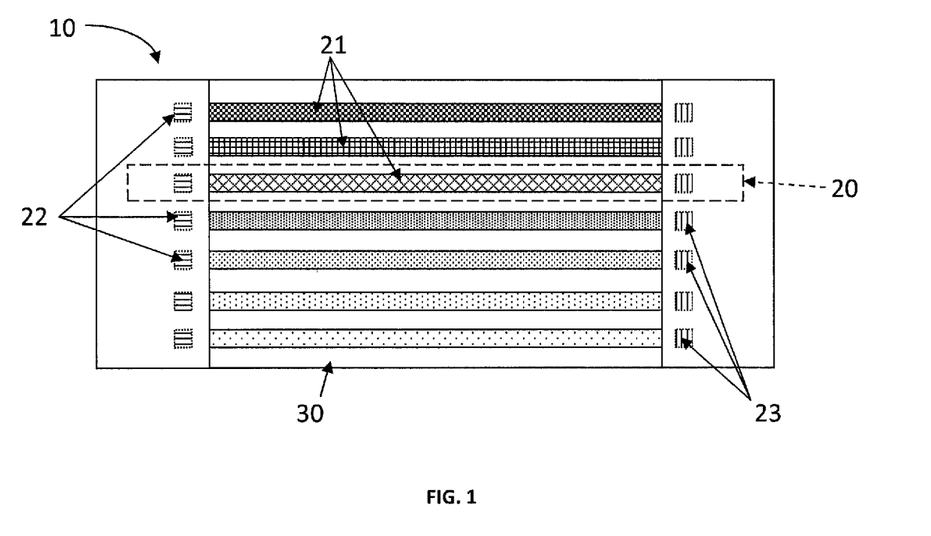
FIG. 1 schematically illustrates an optical multi-analyte (bio)chemical sensor in accordance with one embodiment (top view).

An optical multi-analyte (bio)chemical sensor 10 according to one embodiment is schematically illustrated in FIG. 1 (top view). The sensor 10 comprises a plurality of elongated sensing elements 20 arranged on a substrate 30. Each sensing element comprises a waveguide comprising a waveguide core 21, a light source 22 optically coupled to an input part of the waveguide core 21, and a photodetector 23 optically coupled to an output part of the waveguide core 21. A waveguide core 21 is made of a material comprising a mixture of an optical material and a fluorescent dye sensitive to a predetermined analyte. The sensor can further comprise an optical filter (not shown in FIG. 1) between the output part of the waveguide core 21 and the photodetector 23.

The sensor can further comprise electrical circuitry (not illustrated), e.g. for driving the light sources 22 and for read-out of the photodetectors 23. This electric circuitry can be integrated with the sensor, e.g. with the light sources 22 and with the photodetectors 23. Alternatively the sensor can further comprise electrical connections (e.g. metal tracks) for enabling connection of the sensor to external circuits, e.g. for connection of the light sources 22 to an external driving circuit and/or for connection of the photodetectors 23 to an external read-out circuit.

A sensor 10 according to one embodiment may comprise a single sensing element 20 or more than one, e.g. a plurality of, sensing elements 20. By providing a plurality of sensing elements 20 comprising different fluorescent dyes a multi-analyte sensor can be made.

In one embodiment the different sensing elements 20 may comprise a different fluorescent dye, e.g. to detect different analytes. In one embodiment a same dye can be used in different waveguides, with a different dye concentration in the different waveguides. This may for example increase the dynamic sensing range of the sensor. In one embodiment a same dye can be used in different waveguides, e.g. combined with different filters for the different waveguides, e.g. to measure different parts of the spectrum emitted by the fluorescent dye, allowing to have an indication of the emission spectrum (intensity versus wavelength).

A sensor according to one embodiment preferably comprises a reference sensing element, i.e. a sensing element comprising a waveguide core made of an optical material (e.g. the same optical material as used for fabricating the other sensing elements) not comprising a fluorescent dye. The presence of such a reference sensing element can be advantageous in several aspects. For example, it can be used to assess the effect of external influences such as temperature and humidity, or for example the influence of the light source 22. In operation, the optical power at an output of the reference waveguide (without a dye) can be compared to the optical power at an output of a waveguide comprising a dye. In a certain wavelength range (such as e.g. a wavelength range corresponding to or within the emission spectrum of a fluorescent dye) the optical power at the output of the reference waveguide does not change with the concentration of an analyte, while in the same wavelength range the optical power at the output of the waveguides with a dye does change with the concentration of an analyte.

Figure 2:
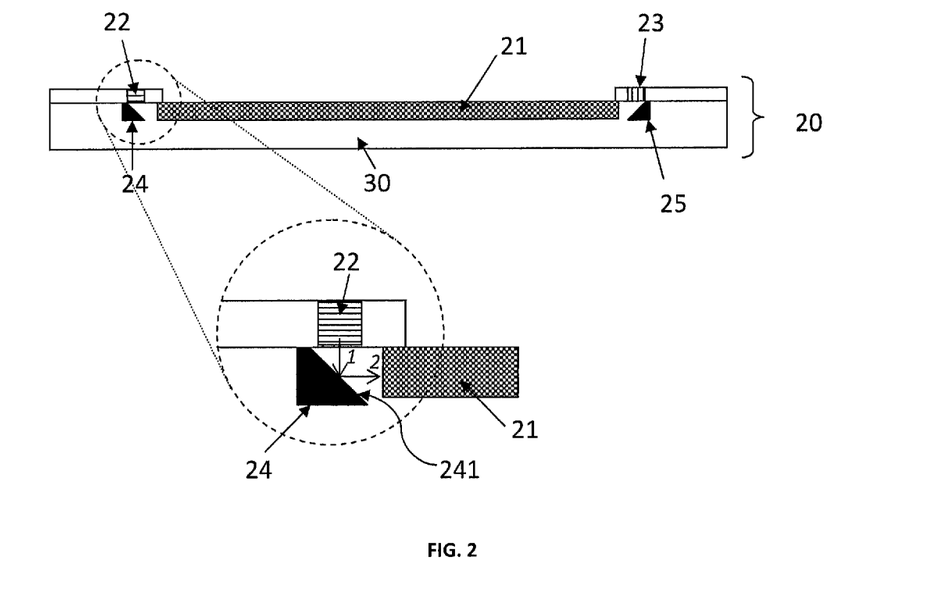
FIG. 2 shows a cross section along a longitudinal direction of a sensing element of a sensor according to one embodiment.

FIG. 2 shows a cross section of a sensor of one embodiment along a longitudinal direction of a sensing element 20. The sensing element 20 comprises a waveguide, the core 21 of the waveguide being made from a material comprising a mixture of an optical material, e.g. optical silicone, and a fluorescent dye. A typical dye concentration is less than 1 w %, but the present disclosure is not limited thereto and other dye concentrations can be used. For example, Nile Red ($C_{20}H_{18}N_2O_2$) is a fluorescent dye that may be used for sensing e.g. toluene, methanol, hexane or 2-butanol. For example, 4-(N,N-Dimethylamine)benzonitrile (DMABN) derivatives with boronic acid and boronate groups can be used as fluorescent dyes for sensing saccharides and fluoride ions. However, the present disclosure is not limited thereto and any other suitable fluorescent dye known to a person skilled in the art may be used.

Preferably the substrate 30 has a refractive index that is lower than the refractive index of the core material in the relevant wavelength ranges used for sensing (e.g. wavelengths of the light sources, wavelength range corresponding to the dye emission spectrum, . . . ), such that the substrate 30 can function as a lower waveguide cladding layer. Alternatively, a substrate 30 having a refractive index equal to or larger than the refractive index of the core material can be used, wherein a (lower) cladding layer is provided on the substrate, the cladding layer having a refractive index lower than the refractive index of the core material. In the example shown in FIG. 2, the ambient functions as an upper waveguide cladding layer. However, the present disclosure is not limited thereto and the sensing element 20 can comprise additionally an upper cladding layer (not illustrated in FIG. 2) on top of the waveguide core 21.

It is an advantage of using optical silicones that they can be (microscopically) porous, thus enabling penetration of analytes into the sensitive core 21, which in turn gives a large interaction area with an analyte to be detected and thus a large sensing area. It is a further advantage of using silicones that they allow forming highly flexible and/or stretchable sensors. This allows using the sensors on curved surfaces such as e.g. gas pipe surfaces (e.g. for leakage detection) and on (or integrated with) flexible/stretchable elements such as for example textile (e.g. protective clothing). It is an additional advantage of using optical silicones that they have less auto-fluorescence as compared to traditional acrylic optical materials. Therefore the characteristics (such as e.g. response, sensitivity, . . . ) of such a sensor are only dependent on the properties of the dye material and not to the properties of the core material since the core material shows no or very limited auto-fluorescence. In addition, optical silicones are highly transparent in the UV-region down to 350 nm. Therefore a large range of wavelengths can be used for sensing, and thus a large variety of fluorescent dyes operating at different wavelengths can be used. Optical silicones also have a potential for biocompatibility.

The presence of a larger sensing area (the area of interaction between an analyte and the material comprising the fluorescent dyes) can result in a better performance (higher sensitivity and higher signal to noise ratio) as compared to prior art sensors. In a sensing element 20 of a sensor according to one embodiment, the length of the waveguide core 21 can be typically a few centimeters, e.g. up to 20 cm, e.g. 10 cm. It is an advantage of longer waveguide cores that they allow more interaction with the analytes to be detected, i.e. the longer the waveguides the larger the sensing area. However, when using a MIMIC approach for fabricating the waveguide cores (as further described) the waveguide core length may be limited for practical reasons.

The sensing element 20 (FIG. 2) further comprises a light source 22, e.g. a light emitting diode, that is optically coupled to an input part of the waveguide core 21 by means of a first coupling element, such as for example a first micromirror 24. In the example shown in FIG. 2 light 1 is emitted from the light source 22 in a direction substantially orthogonal to the plane of the substrate 30. The light is reflected by the first micromirror 24 having a reflecting surface 241 oriented at 45° relative to the plane of the substrate 30, and being positioned relative to the waveguide core 21 in such a way that the reflected light 2 is coupled into the waveguide core 21. Other coupling elements such as for example an optical grating structure or a prism structure can be used for optically coupling the light source 22 to the input part of the waveguide core 21. In other embodiments a light source can be used that emits light in a direction substantially parallel with the plane of the substrate 30. For example, a side-emitting light emitting diode can be used. In such embodiments, light emitted by the light source can be coupled directly (in-plane) to the waveguide core without the need for providing a first coupling element.

The light source 22 is selected such that it emits light in a wavelength range within or overlapping with the excitation spectrum of the fluorescent dye (sensitive to a predetermined analyte to be detected) in the corresponding waveguide core 21. In addition, the light source 22 may also be selected such that there is no or limited light emission in the wavelength range corresponding to the emission spectrum of the fluorescent dye.

The sensing element 20 further comprises a photodetector 23, e.g. a photodiode, optically coupled to an output part of the waveguide core 21, for example by means of second coupling element such as for example a second micromirror 25. In the example shown in FIG. 2, light that is emitted from the waveguide core 21 in a direction substantially parallel to the plane of the substrate 30 is reflected at a 45° surface of the second micromirror 25. The reflected light (in a direction substantially orthogonal to the plane of the substrate) is detected by the properly positioned photodetector 23. Other means such as for example an optical grating structure or a prism structure can be used for optically coupling the photodetector 23 to the output part of the waveguide core. In other embodiments a photodetector 23 can be used that detects light in a direction substantially parallel with the plane of the substrate. In such embodiments, light exiting the waveguide core can be coupled directly (in-plane) to the photodetector without the need for providing a second coupling element. However, integration of this type of photodetectors may be more difficult.

The photodetector 23 is selected such that it is sensitive in a wavelength range corresponding to the emission spectrum of the fluorescent dye. In between the waveguide core 21 and the corresponding photodetector 23 an optical filter can be provided for filtering out non-desired wavelengths, such as for example the excitation wavelengths from the light source 22, and thus improving the signal to noise ratio of the sensing element.

For example, an integrated multilayer filter can be used. Such multilayer filter can for example be provided at a front side (light receiving side) of the photodetector 23. Alternatively, a filter can be provided that is based on mixing suitable dyes with the material of the waveguide core, as for example reported by C. L. Bliss et al. in "Integrated wavelength-selective optical waveguides for microfluidic-based laser-induced fluorescence detection," Lab Chip (2008), 8: 143-151. In such embodiments (schematically illustrated in FIG. 3) the waveguide core 21 of the sensing elements 20 comprises a main part 211 comprising a gas sensitive fluorescent dye and a filter part 212 (at the output part of the waveguide core) comprising a wavelength selective absorbing dye acting as a filter, e.g. for the excitation wavelengths. The dye of the filter can for example be selected for selectively attenuating stray excitation light while efficiently transmitting the fluorescence signal.

In the example shown in FIG. 2 the substrate 30 functions as a lower cladding layer and the environment (ambient) forms the upper cladding of the waveguide structure. It is an advantage of this approach that the waveguide core 21 is directly exposed to the environment, which may comprise analytes to be detected, and therefore offers a direct interaction of the analytes with the dyes and thus a good sensitivity. In addition to mixing the fluorescent dyes with the optical material forming the waveguide core, a surface layer comprising fluorescent dyes can be provided on top of the waveguide core 21, thereby allowing an even faster and more sensitive response.

However, the present disclosure is not limited thereto. For example, an additional layer can be provided on the waveguide core 21 for forming an upper cladding layer. This upper cladding layer is preferably porous, i.e. allowing an analyte to be detected to pass through it. It is an advantage of providing an upper cladding layer that it may help avoiding contamination (e.g. due to dust particles) of the waveguide core, which may influence the sensor operation and/or the sensor performance.

In operation, light is emitted by the light source 22 and coupled into the core 21 of a waveguide, the core comprising a fluorescent dye with a predetermined excitation spectrum and sensitive to a predetermined analyte. The fluorescent dye absorbs light of a first wavelength or first wavelength range within its excitation spectrum and re-emits part of the absorbed energy at a second wavelength or in a second wavelength range different from the first wavelength range. The intensity and/or the wavelength of the emitted energy depend both on the fluorescent dye and on the chemical environment of the fluorescent dye. In one embodiment, the optical material, e.g. optical silicone, used for forming the waveguide core 21, is a porous material allowing penetration of an analyte to be detected through the pores towards the dye. Thus, upon diffusion of an analyte to be detected into the pores of the waveguide core, the emission spectrum of the fluorescent dye changes. This change in emission spectrum comprises a shift in emission wavelengths and/or a change in emitted optical energy (total emitted energy or energy emitted at a specific wavelength).

A change in fluorescence with the presence of an analyte can be detected either based on a wavelength shift or based on a change in intensity.

Figure 9:
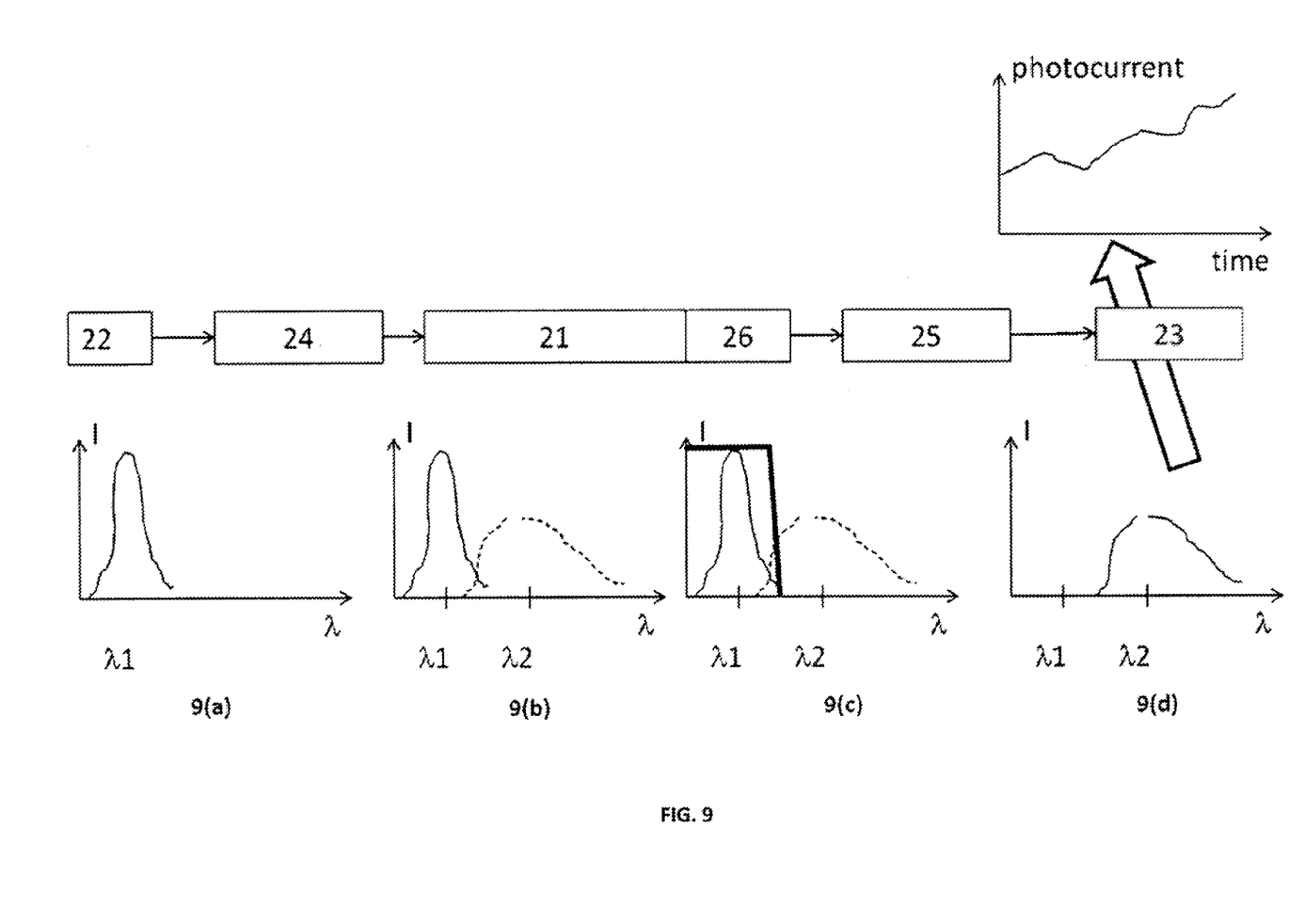
FIG. 9 illustrates an example of intensity based detection using a sensor of one embodiment.

FIG. 9 illustrates an example of intensity based detection using a sensor of one embodiment. FIG. 9(a) shows the spectrum (intensity as a function of wavelength) emitted by a light source 22, with a maximum intensity at a first wavelength $\lambda_1$. At least part of the light emitted by the light source 22 is absorbed by the fluorescent dye present in the waveguide core 21. FIG. 9(b) shows an emission spectrum (dashed curve) of the fluorescent dye, with a maximum intensity at a second wavelength $\lambda_2$ different from (higher than) $\lambda_1$. This emission spectrum depends for example on the type of analyte being present in the environment and on the analyte concentration. In FIG. 9(c) the use of a filter 26 for filtering out the spectrum of the light source 22 is illustrated (bold line). This results in the spectrum shown in FIG. 9(d) being detected by a photodetector 23. In the example shown, the photodetector measures the total optical power (integrated over all wavelengths of the emission spectrum), resulting in a photocurrent through the photodetector. This photocurrent can be measured as a function of time. As an alternative to measuring the total optical power, the optical power may be measured at a single wavelength or in a wavelength range smaller than the range of the emission spectrum.

Figure 10:
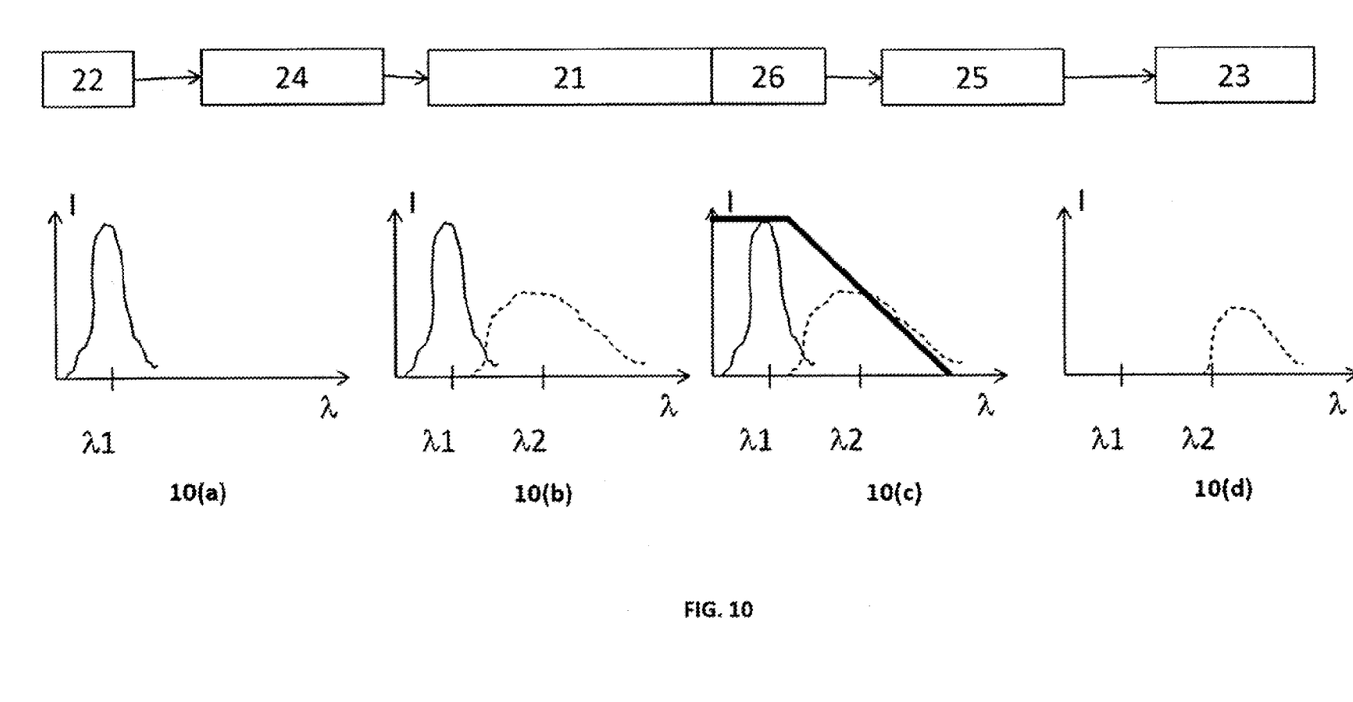
FIG. 10 illustrates an example of wavelength based detection using a sensor of one embodiment.

FIG. 10 illustrates an example of wavelength based detection using a sensor of one embodiment. FIG. 10(a) shows the spectrum (intensity as a function of wavelength) emitted by a light source 22, with a maximum intensity at a first wavelength $\lambda_1$. At least part of the light emitted by the light source 22 is absorbed by the fluorescent dye present in the waveguide core 21. FIG. 10(b) shows an emission spectrum (dashed curve) of the fluorescent dye, with a maximum intensity at a second wavelength $\lambda_2$ different from (higher than) $\lambda_1$. This emission spectrum depends for example on the type of analyte being present in the environment and on the analyte concentration. In FIG. 10(c) the use of a filter 26 for filtering out the spectrum of the light source 22 is illustrated (bold line), wherein the filter has a sloped characteristic in a wavelength range corresponding to the emission spectrum of the fluorescent dye. Therefore, a horizontal shift (i.e. a wavelength shift) of the emission spectrum of the fluorescent dye results in a shift of the power transmitted to and measured by the photodetector 23 (FIG. 10(d)). For example, the photodetector 23 can measure the total optical power after filtering, resulting in a photocurrent through the photodetector. A shift of the emission spectrum as a function of the wavelength results in a different power measured by the photodetector. As an alternative to measuring the total optical power, the optical power may be measured at a single wavelength or in a wavelength range smaller than the range of the emission spectrum.

An exemplary method based on a MIMIC (micromoulding in capillaries) approach is further described for fabricating a sensor according to one embodiment. However, the present disclosure is not limited thereto and other suitable fabrication methods known to a person skilled in the art can be used, such as for example methods comprising embossing, photolithography, laser ablation and/or etching.

Figure 4:
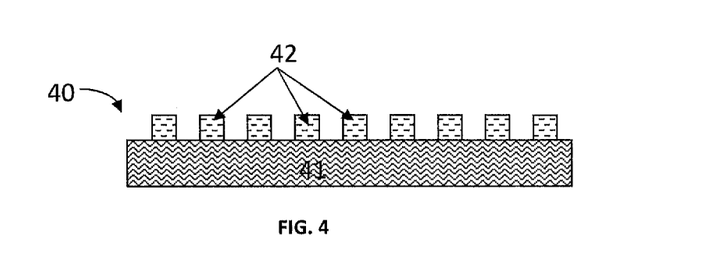
FIG. 4 shows a master mold as used in a fabrication process of a patterned sensor substrate according to one embodiment.

In a first step a reusable master mold is fabricated, for example by forming SU-8 photoresist features on a rigid substrate such as a silicon substrate, e.g. using photolithography. Such a master mold 40 is schematically illustrated in FIG. 4, showing a silicon substrate 41 with a photoresist pattern 42 on a substrate surface. The pattern thus formed corresponds to the pattern of waveguide cores to be formed (replicated) in a later phase of the process. Other materials can be used for forming the master pattern structure. For example, substrates other than a silicon wafer can be used, and other materials than SU-8 can be used for forming the patterns. Also flexible substrates can be used. For example, the master mold can comprise a foil with embossed features, allowing roll-to-roll processing.

Figure 5:
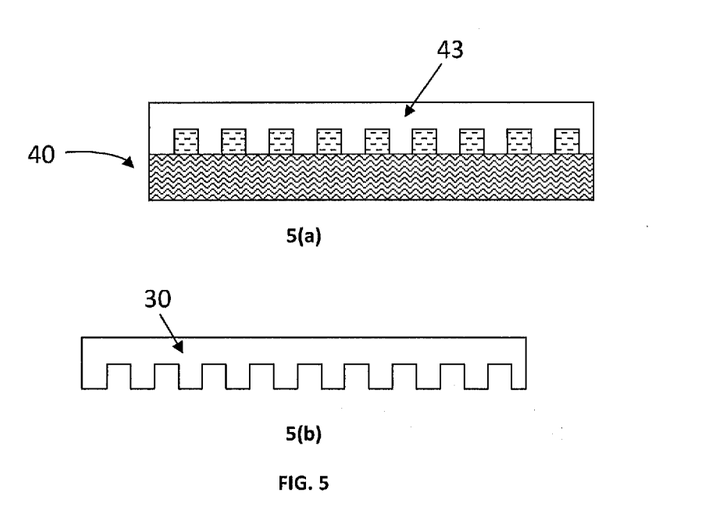
FIG. 5(a) and FIG. 5(b) illustrate a fabrication process of a patterned sensor substrate according to one embodiment.

Using the master mold 40, patterned substrates 30 are fabricated, the patterned substrates 30 comprising channels where in a later phase of the fabrication process the waveguide cores 21 of the sensing elements 20 will be provided. A method that can be used for forming the patterned substrates 30 based on replica molding is schematically illustrated in FIG. 5. A layer 43 of PDMS (polydimethylsiloxane, such as for example Sylgard 184) is provided on the master mold 40, for example by spin coating (FIG. 5(a)). After curing of the PDMS layer 43 (e.g. thermal curing or curing at room temperature), the cured layer is peeled off from the master mold 40, thus forming a patterned PDMS substrate 30 (FIG. 5(b)). The master mold 40 is reusable, i.e. it can be used for fabricating a plurality of patterned substrates 30.

Figure 6:
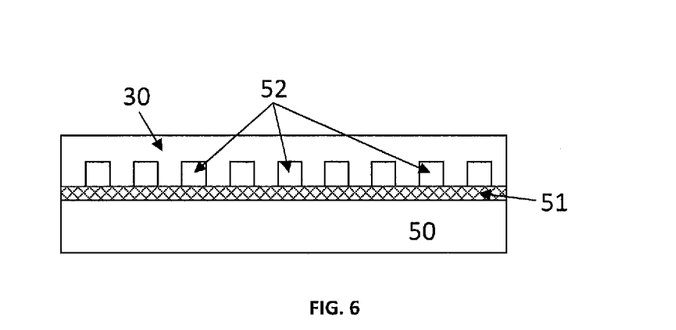
FIG. 6, FIG. 7, and FIG. 8 illustrate a fabrication process for forming waveguides in accordance with one embodiment.

Next, as illustrated in FIG. 6, the patterned PDMS substrate 30 is bonded to a plane substrate such as a plane glass substrate 50 covered with a release layer 51 such as for example a polyvinyl acetate (PVA) layer. The patterned substrate 30 is oriented with its patterned side towards the glass substrate 50, such that a plurality of channels 52 is formed between the plane glass substrate 50 and the patterned PDMS substrate 30, the channels being closed at all sides except at an inlet side and at an outlet side. The channels 52 can for example have a depth (i.e. a size in a direction substantially orthogonal to the plane of the substrate 50) in the range between 1 micrometer and 100 micrometer, e.g. in the order of 50 micrometer and a width (i.e. a size in a direction substantially parallel to the plane of the substrate 50) in the range between 1 micrometer and 1 mm, e.g. in the order of 500 micrometer. Bonding the patterned substrate 30 to a plane substrate 50 can for example comprise plasma bonding, wherein the surfaces to be bonded are first exposed to an oxygen plasma or an oxygen containing plasma and then brought into physical contact to induce the bonding process. Instead of a glass substrate 50, other rigid or flexible substrates can be used, such as for example a PET (polyethylene terephthalate) foil or a PEN (polyethylene naphthalate) foil. In embodiments of the present disclosure the patterned substrate can also be bonded to a plane substrate 50 covered with a release layer 51, the release layer 51 being covered with an additional layer that can act as an upper cladding layer in the final device.

Figure 7:
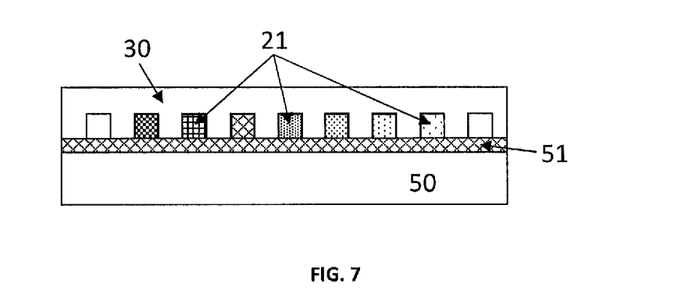

After finishing the bonding step, each of the plurality of channels 52 is filled by capillary forces with an optical silicone mixed with a fluorescent dye for forming waveguide cores 21. This filling step comprises, for each channel, providing a small amount of a (liquid) optical silicone mixed with a fluorescent dye at an inlet side of the channel. The amount of optical silicone depends on the size of the channels and is selected to be sufficient for completely filling the channels. The optical silicone can for example be a type of PDMS having a higher refractive index than the PDMS used for the patterned substrate 30, and having a viscosity preferably lower than 1000 mPAs. Preferably the working time is sufficiently long to allow filling of the channels before the material starts hardening (curing). The channel is filled with this material by capillary forces. The speed of filling depends on the channel dimensions and on the viscosity of the liquid. When the channel is completely filled, the core material is cured (e.g. thermally cured), thereby forming a waveguide core 21. FIG. 7 illustrates the structure after filling of the channels with different materials.

Figure 8:
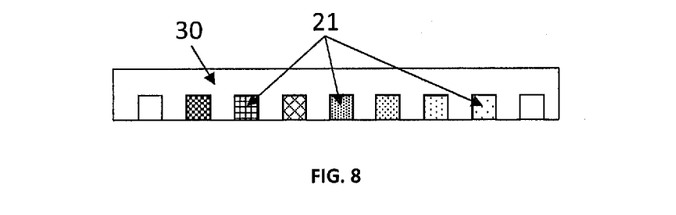

Next, the plane glass substrate 50 is removed, e.g. by water treatment for dissolving the release layer 51. This results in a structure comprising the PDMS mold or patterned substrate 30 having channels filled with optical silicones. In this way a plurality of waveguides is formed, the patterned PDMS substrate 30 for example having the function of (bottom) cladding layer, and the optical silicones mixed with fluorescent dyes forming the core 21 of the waveguides (FIG. 8).

Figure 3:
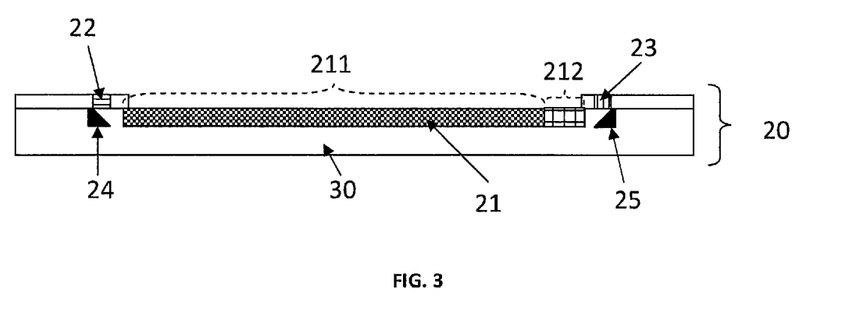
FIG. 3 shows a cross section along a longitudinal direction of a sensing element of a sensor according to one embodiment wherein the sensing element comprises a filter at an output part of the waveguide core.

In embodiments wherein the filter at the front side of the photodetector 23 is formed by providing a wavelength selective absorbing dye in the filter part 212 of a waveguide core 21, as illustrated in FIG. 3, the channel can be divided in a first part and a (smaller) second part separated from the first part. The first part corresponds to the main part of the waveguide core and the second part corresponds to the filter part of the waveguide core. At the interface between the first part and the second part a channel outlet can be provided for both channel parts, to allow air to escape from the channel parts during filling. It is an advantage of providing such channel outlets that channel filling can be faster. It is an additional advantage that both materials remain separated and that the dimensions of both parts (i.e. the main part 211 and the filter part 212) are well controlled.

In one embodiment of a sensor wherein the waveguide cores 21 are covered by an upper cladding layer, instead of bonding the patterned PDMS substrate 30 to a plane substrate 50 with a release layer 51, the patterned PDMS substrate 30 is directly bonded to a second, plane PDMS substrate without a release layer in between. The second, plane PDMS substrate then remains in the final device and has the function of an upper cladding layer.

The MIMIC approach used here differs from prior art MIMIC approaches, wherein the patterned PDMS substrate is used as a mold for replicating the pattern of the master mold on a substrate. In such prior art approach, the patterned PDMS substrate or mold is provided on a substrate and the openings thus created between the substrate and the polymer replica are filled with a liquid material by capillary filling. After curing, the PDMS mold (patterned substrate) is removed such that it can be reused. In one embodiment the PDMS mold is not removed after filling the openings and curing the core material. Instead the plane substrate can be removed, and the PDMS mold (patterned substrate) is used in the final device as a substrate.

After forming the plurality of waveguides, additional components such as light emitting devices, micromirrors, photodetectors, filters, driving circuitry and read-out circuitry need to be integrated with the waveguides.

Different approaches can be used for the integration of these additional components with the waveguide structures.

For example, the sensor can be made of two parts later bonded together: a first part (further referred to as 'waveguide part') comprising the waveguides and a second part (further referred to as 'optoelectronics part') comprising the optoelectronic components and electrical circuitry. If both parts are bonded in a releasable way, the waveguide part could be disposable and the optoelectronics part could be reusable. However, both parts can also be permanently bonded, e.g. by plasma bonding.

The coupling elements (such as mirrors or gratings) for coupling light from the light sources to the waveguide cores and from the waveguide cores to the photodetectors can be integrated with the waveguide part. When bonding both parts together, the light sources and the photodetectors are then aligned with respect to the corresponding coupling elements, e.g. micromirrors. This approach allows an accurate mirror placement. However the alignment of the optoelectronic components may be difficult because aligning and gluing or bonding need to be done simultaneously. Alternatively, the coupling elements (such as mirrors or gratings) for coupling light from the light sources to the waveguide cores and from the waveguide cores to the photodetectors can be integrated with the optoelectronics part. In this approach the coupling elements, e.g. micromirrors, are first aligned with the optoelectronic components and fixed using an accurate fine-pitch component placer. This is followed by alignment to the waveguides and gluing. It is an advantage of this approach that the pre-aligned mirrors can serve as alignment aids for proper positioning with respect to the waveguides cores.

The foregoing description details certain embodiments of the disclosure. It will be appreciated, however, that no matter how detailed the foregoing appears in text, the disclosure may be practiced in many ways. It should be noted that the use of particular terminology when describing certain features or aspects of the disclosure should not be taken to imply that the terminology is being re-defined herein to be restricted to including any specific characteristics of the features or aspects of the disclosure with which that terminology is associated.

While the above detailed description has shown, described, and pointed out novel features of the disclosure as applied to various embodiments, it will be understood that various omissions, substitutions, and changes in the form and details of the device or process illustrated may be made by those skilled in the technology without departing from the spirit of the disclosure.

What is claimed is:

1. An optical fluorescence-based sensor comprising at least one sensing element, the at least one sensing element comprising a waveguide, the waveguide comprising:
    a waveguide core formed in a substrate;
    a light source integrated into the waveguide on the substrate, the light source optically coupled to an input part of the waveguide core; and
    a photodetector integrated into the waveguide on the substrate, the photodetector optically coupled to an output part of the waveguide core, the waveguide core being made of a material comprising a mixture of an optical material and a fluorescent dye, wherein the fluorescent dye has an excitation spectrum and an emission spectrum, the emission spectrum depending on the presence of an analyte to be detected, wherein the light source is selected such that it emits light in a first wavelength range overlapping at least partly with the excitation spectrum of the fluorescent dye, and wherein the photodetector is selected such that it is sensitive in a wavelength range corresponding to the emission spectrum of the fluorescent dye.

2. The optical fluorescence-based sensor according to claim 1, wherein the optical material is a porous material allowing penetration of an analyte to be detected through the pores towards the fluorescent dye.

3. The optical fluorescence-based sensor according to claim 1, wherein the optical material is a flexible and/or stretchable material.

4. The optical fluorescence-based sensor according to claim 1, wherein the optical material of the waveguide core comprises an optical silicone.

5. The optical fluorescence-based sensor according to claim 1, wherein the at least one sensing element further comprises an optical filter in between the output part of the waveguide core and the photodetector.

6. The optical fluorescence-based sensor according to claim 1, further comprising a plurality of sensing elements, each of the sensing elements comprising a different fluorescent dye.

7. The optical fluorescence-based sensor according to claim 1, further comprising a reference sensing element comprising a waveguide core made of a material comprising the same optical material as used for fabricating the at least one sensing element but not comprising a fluorescent dye, the optical sensor being provided to, in operation, compare the optical power at the output of the reference sensing element to the optical power at the output of the at least one sensing element with the waveguide comprising a fluorescent dye.

8. The optical fluorescence-based sensor according to claim 1, wherein a coupling element optically couples the light source to the input part of the waveguide core and/or couples the photodetector to the output part of the waveguide core.

9. The optical fluorescence-based sensor according to claim 8, wherein the coupling element comprises any one of a micromirror, a prism, or a grating structure.

10. A method for fabricating the optical fluorescence-based according to claim 1, the method comprising:
    providing a master mold comprising a pattern corresponding to the pattern of at least one waveguide core to be formed;
    fabricating a patterned substrate using the master mold as a template;
    bonding the patterned substrate to a plane substrate, thereby forming a plurality of channels between the patterned substrate and the plane substrate;
    filling the plurality of channels with a material comprising a mixture of an optical material and a fluorescent dye; and
    curing the material, thereby forming a plurality of waveguide cores.

11. The method according to claim 10, wherein the method further comprises integrating at least one light source and optically coupling the light source to an input part of the waveguide core by means of a first coupling element and/or integrating at least one photodetector and optically coupling the photodetector to an output part of the waveguide core by means of a second coupling element.

12. The method according to claim 11, wherein the first and/or the second coupling element comprises a micromirror, a grating, or a prism.

13. A method of detecting an analyte using the optical fluorescence-based sensor according to claim 1, the method comprising:
    emitting light from the light source;
    absorbing, in the fluorescent dye, light of the first wavelength range according to the excitation spectrum of the fluorescent dye;
    re-emitting part of the absorbed energy in a second wavelength range different from the first wavelength range according to the emission spectrum of the fluorescent dye; and
    detecting, in the photodetector, at least part of the re-emitted part of the absorbed energy coupled from the waveguide core into the photodetector, wherein the photodetector detects a change in the emission spectrum of the fluorescent dye due to the presence of the analyte.

14. An optical fluorescence-based sensor comprising at least one sensing element comprising a waveguide, the waveguide comprising:
    a waveguide core, a light source, and a photodetector integrated on a substrate;
    means for optically coupling the light source to an input part of the waveguide core; and
    means for optically coupling the photodetector to an output part of the waveguide core, the waveguide core being made of a material comprising a mixture of an optical material and a fluorescent dye, wherein the fluorescent dye has an excitation spectrum and an emission spectrum, the emission spectrum depending on the presence of an analyte to be detected, wherein the light source is selected such that it emits light in a first wavelength range overlapping at least partly with the excitation spectrum of the fluorescent dye, and wherein the photodetector is selected such that it is sensitive in a wavelength range corresponding to the emission spectrum of the fluorescent dye.

15. The optical fluorescence-based sensor according to claim 14, wherein the means for coupling the light source to the input part of the waveguide core comprises a micromirror, a prism, or a grating structure.

16. The optical fluorescence-based sensor according to claim 14, wherein the means for coupling the photodetector to the output part of the waveguide core comprises a micromirror, a prism, or a grating structure.

* * * * *